United States Patent [19]
Wu

[11] Patent Number: 4,972,720
[45] Date of Patent: Nov. 27, 1990

[54] THERMAL TECHNIQUE FOR DETERMINING INTERFACE AND/OR INTERPLY STRENGTH IN COMPOSITES

[75] Inventor: Wen-li Wu, Rockville, Md.

[73] Assignee: The United States of America as represented by the Secretary of Commerce, Washington, D.C.

[21] Appl. No.: 409,854

[22] Filed: Sep. 20, 1989

[51] Int. Cl.$^5$ ............................................. G01N 29/04
[52] U.S. Cl. ........................................ 73/801; 374/57
[58] Field of Search ................. 73/582, 801, 587, 588, 73/788; 374/46, 57

[56] References Cited

U.S. PATENT DOCUMENTS 4,004,456 1/1977 Vahaviomos .
4,024,522 5/1977 Clark .
4,543,486 9/1985 Rose .

FOREIGN PATENT DOCUMENTS 0705330 12/1979 U.S.S.R. ................................ 73/801
1374101 2/1988 U.S.S.R. .
1523295 8/1988 United Kingdom .................. 73/582

OTHER PUBLICATIONS

Webster's II New Riverside University Dictionary 1988, Houghton Mifflin Company (pp. 342, 874).

Primary Examiner—Robert Raevis
Attorney, Agent, or Firm—Thomas Zack; Alvin J. Englert; Michael S. Gzybowski

[57] ABSTRACT

A method and apparatus for characterizing bonding properties in compositions which utilizes thermal energy to cause controlled debonding of interface and/or interply bonds. Debonding events resulting from the controlled debonding are detected and utilized to characterize the interface and/or interply properties of the composition.

19 Claims, 7 Drawing Sheets

THERMAL TECHNIQUE FOR DETERMINING INTERFACE AND/OR INTERPLY STRENGTH IN COMPOSITES

Technical Field

The present invention relates to a technique for characterizing the interface and/or interply properties of composites. In particular, the present invention relates to a thermal technique that disrupts interface and/or interply bonds in composites and characterizes the bonds by monitoring debonding events.

Background Art

Physical properties of composites depend strongly on the interface between the filler and the matrix which make up the composites. Known sonic scan techniques have been used to detect voids or cracks at the interfaces of composites, but they cannot be used to determine the bonding strengths. Other techniques such as dynamic mechanical tests have been tried, but are not conclusive.

Some in vitro techniques exist for measuring and evaluating the interface strength of laboratory samples of composites. Micro-indentation tests which push in the fiber, fiber pull-out, and single fiber coupon tests are the popular in vitro techniques. However, all of these tests are rather time consuming and tedious, and special test specimens have to be prepared. Moreover, these tests are disadvantageous in that they cannot be adapted easily to "real world" composites having complex structures.

Previous optical and acoustic methods have been utilized to detect certain preexisting flaws, debond areas or compositional variations. Such methods have not been directed at debonding fiber-matrix interfaces or the interply regions or to determine bonding strengths.

The present invention is a novel technique which allows for investigation and characterization of interface and interply properties of composites.

Disclosure of the Invention

It is accordingly one object of the present invention to provide for a method of characterizing interface and/or interply properties of composites.

Another object of the present invention is to provide for a method for causing and monitoring interface and/or interply debonding of composites.

A further object of the present invention is to provide for a method for thermally causing interface and/or interply debonding of composites and monitoring the debonding so as to determine bond strengths.

An even further object of the present invention is to provide an apparatus for characterizing the interface and/or interply properties of composites.

A still further object of the present invention is to provide an apparatus for causing debonding of the interface and/or interply of composites, for monitoring the debonding events and for characterizing the interface and/or interply properties of the compositions.

Brief Description of Drawings

The present invention will now be described with reference to the annexed drawings, which are given by way on non-limiting examples only in which.

Best Mode for Carrying out the Invention

The present invention is relates to a method for characterizing interface and interply properties of composites which utilizes various heating and/or cooling techniques to generate or induce local interfacial debonding events The resulting debonding is monitored via an appropriate means such as an acoustic sensor which senses acoustic signals generated as a result of the debonding. Characteristics of the debonding as monitored by means of the acoustic signals are related to interface and interply strength.

For most compositions the thermal expansion coefficients between the filler and the matrix are different. Heating or cooling can cause debonding at the interface due to the build-up of thermally induced stress. This difference in thermal expansion coefficients is very pronounced in polymer matrix composites.

At temperatures above the polymer's glass transition temperature the thermal expansion coefficient can be higher than that of the filler by a few orders of magnitude. For a given matrix and filler combination, the temperature at which debonding occurs depends on the bonding strength at the interface; the greater the interface strength the higher temperature for the debonding to occur. By monitoring the debonding temperature and other interface failure characteristics, it has been discovered that the interface strength can be determined according to the present invention.

The technique of the present invention is applicable to a variety of composites, but is particularly applicable to polymer matrix composites which include a polymer matrix with reinforcing filler material, such as graphite fibers For the type of composite investigated by the present technique thermal stress exists not only in at the fiber/matrix interface, but also at the inter-lamellar or interply layer.

Within each ply of polymer matrix composites all the fibers are oriented in the same direction. This orientation direction changes only between plies. Thermal expansion occurs mainly at directions perpendicular to the fibers within each ply. Due to the mismatch in the direction of preferred thermal expansion between plies, large interply thermal stresses can also be induced and these stresses can lead to failure. Hence, the present technique can be utilized to monitor the interply strength as well as the fiber-matrix strength.

The necessary heat can be supplied by a number of possible sources including resistance heaters, open flames, hot gases, microwaves or other radiative sources. A particularly useful heat source for purposes of the present invention includes a laser source such as argon or $CO_2$ laser. In further embodiments of the present invention it was found that local cooling of the composites and combinations of local heating and cooling were effective to produce desired debonding. Cooling can be achieved by utilizing conventional cooling fluids, gases, liquids, etc.

In a preferred embodiment of the present invention the debonding events were monitored utilizing an acoustic emission detecting device. Instead of measuring the thermal stress which depends on the local temperature and local temperature gradients, the power level of the heating device at which debonding occurred was taken as an index of the debonding stress.

In further embodiments of the present invention other suitable means for detecting debonding events include optical sensors, holography means and the like which are capable of detecting physical changes which occur during debonding and after debonding. In the later regard, it was observed that samples with weak interfacial strengths formed blisters when locally heated. These blisters can be detected and monitored by optical means. In instances wherein the physical changes are slight or occur below the surfaces they can also be detected by physical means such as measuring the softening of the surface which results from the debonding.

The thermal debonding process can be varied to application of periodic, cyclic, constant or ramped energies. In one embodiment wherein a laser power was utilized, the laser power was focused on a fixed point over a predetermined period of time of about five seconds. Debonding and resulting debonding events can also be achieved by ramping the laser power at a certain rate and while detecting the onset of an acoustic or optical signal as a function of the power level. Likewise, the laser could be scanned over a predetermined power setting over a wide area. Various schemes such as these could also be combined.

The detected debonding emission signal(s) can be correlated to the thermal power levels in a number of ways including amplitude of the emissions signal, counts, energy, rise time, duration and the like. In a exemplary illustration the area under acoustic signal curves was correlated to the power levels of a laser and related to properties of the interface and interply of sample composites.

Figure 1:
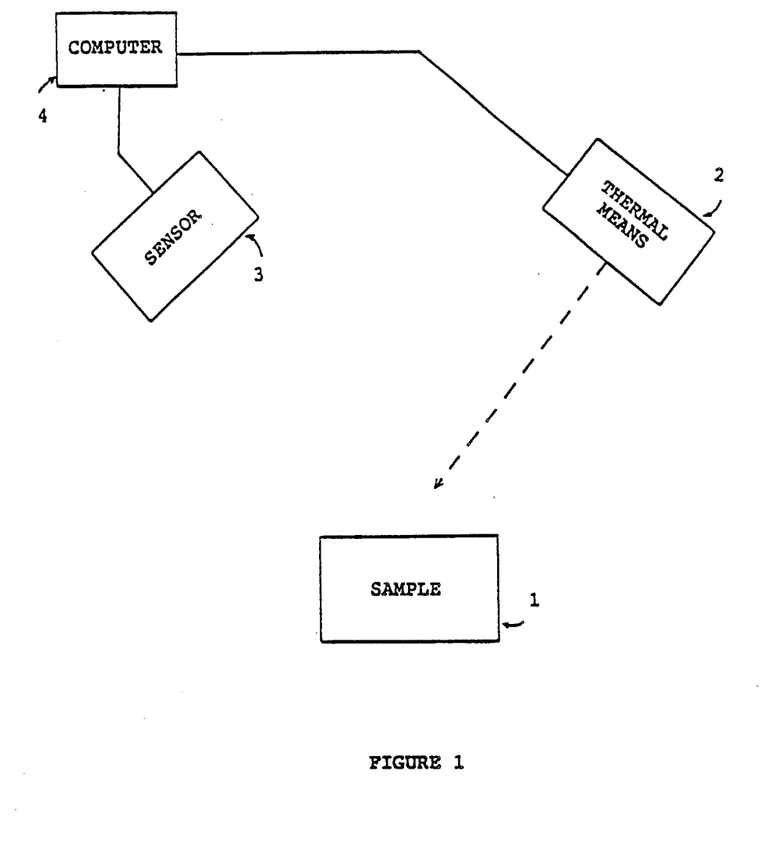
FIG. 1 is a schematic illustration of the apparatus of the present invention.

The basic apparatus utilized in the present invention is schematically illustrated in FIG. 1. The apparatus includes a thermal heating and/or cooling means 2, which can be focused on composite sample 1. Also, included is one or more sensor means 3, which may detect debonding events including surface characteristics of sample. Not illustrated are conventional means to monitor input and output from the thermal means 2 and sensor means 3, and means to correlate data, e.g. computer means 4.

In the course of the present invention it has been discovered that in certain polymer composites which are identical in their composition, but different in their interfacial strengths, the ones with weaker interfaces yield more acoustic output than the stronger ones. This observation is confirmed in the following examples which are given for illustration purposes only. However, this finding may be more reliable for teaching that different interfacial strengths can be detected and discerned. In this regard, it is believed that at least in some instances, the relationship between interfacial strengths and acoustic output may be opposite to that observed in the following examples.

Examples

In each of the following examples the heating source was an Argon ion laser of the continuous wave type. Using a lens of 6 cm. focal length, the beam was focused on the top surface of the composite sample for 5 seconds and then was shut off completely. The acoustic signal was detected using an acoustic sensor (Series 3000 system of Physical Acoustic Corporation, Princeton, N.J.) both during and after the heating period. All the electronic settings stayed unchanged throughout the experiment. The acoustic sensor was placed 5 cm. from the heating spot along the fiber direction of the top ply.

The composite samples utilized in these examples was a matrix made from a stoichiometric mixture of a diglycidyl ether of bisphenol-A (Epon 828, Shell Chemical Co.) and meta-phenylene diamine (m-PDA, Aldrich Chemical Co.). This matrix material is one of the most commonly used epoxies. The fibers used were two polyacrylonitrile based graphite fibers, AU-4 and AS-4 and were both purchased from Hercules, Inc. These two fibers differ only in their surface treatments. Composite samples of 12 plys were made according to the scheme of L. T. Drzal et al (J. Adhesion, 16, 133-152 (1983)). The resultant samples had an interfacial shear strength of 5.4 ksi and 9.9 ksi for the AU-4 and AS-4 composites respectively.

Example 1

In this example samples having a 0/90 ply orientation were subjected to the laser heating process described above. The total acoustic energy for these compositions (defined as a function of the area under the amplitude-time curve: Technical Manual Rev. 1-3-80, page 3, Physical Acoustic Corp., Princeton, N.J. 08540) is plotted as a function of the laser power in FIG. 1.

Figure 2:
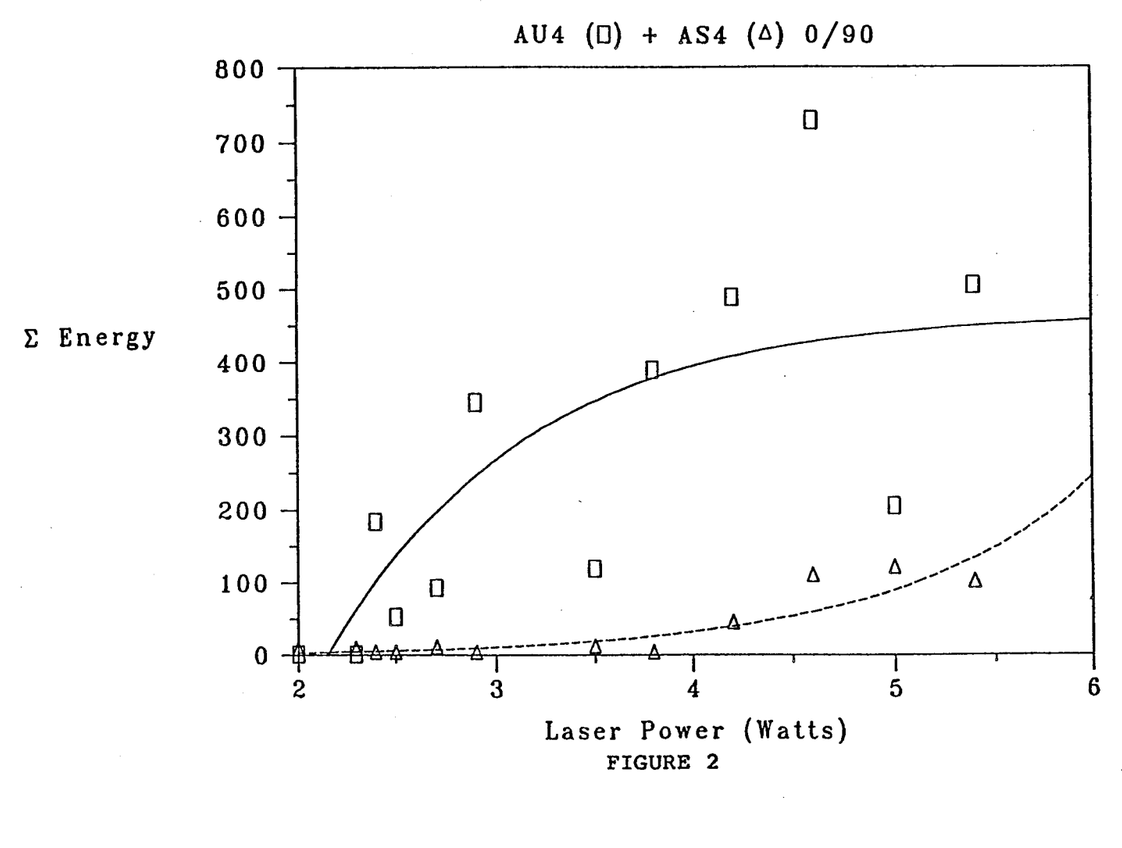
FIGS. 2-6 are a graphs which illustrate the relationship between acoustic energy emissions and laser power for various composite samples.

As illustrated in FIG. 2, the minimum laser power to create an acoustic signal is 2 and 4 watts for the AU-4 and AS-4 samples respectfully. As observed, the acoustic energy level is higher for AU-4 than AS-4 for all the laser power levels tested in this example. Thus, it is clear that composites in this example with weaker interfaces tend to be more noisy under this test condition and vice versa.

Example 2

Figure 3:
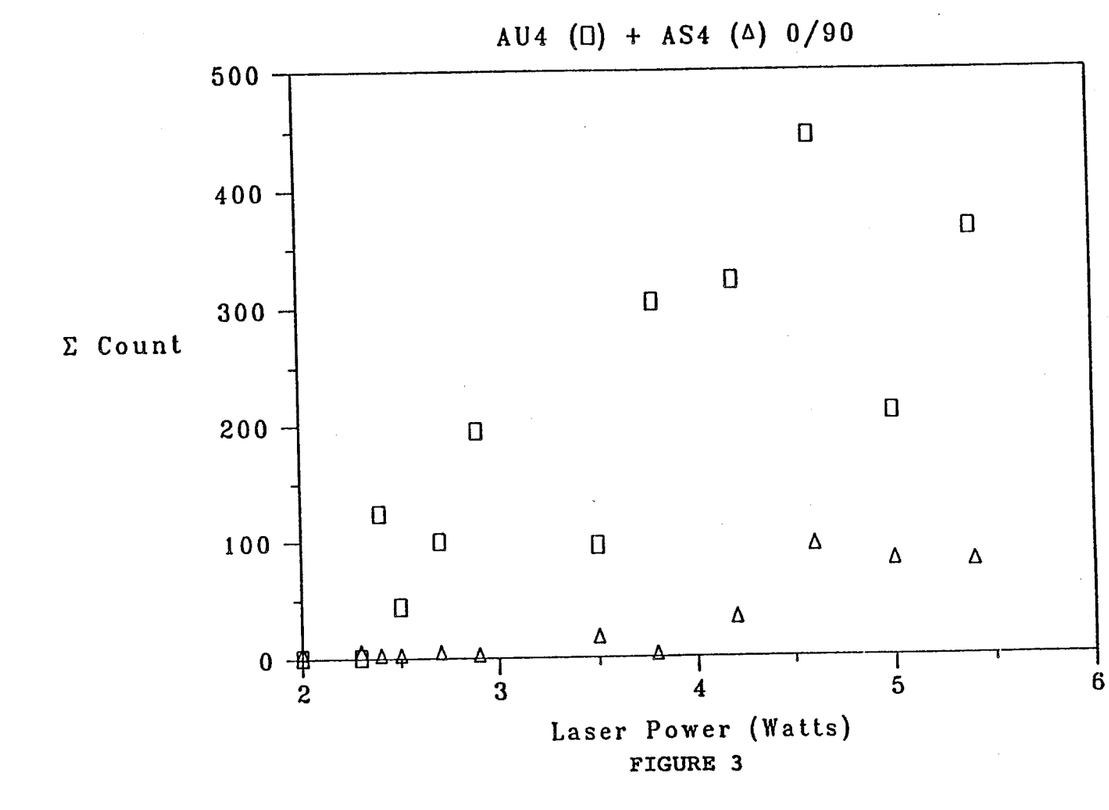

In this example, samples having a 0/90 ply orientation were subjected to the laser heating process discussed above. In FIG. 3 the number of cumulative acoustic events is plotted versus laser power. A trend similar to that discover in Example 1 is observed in FIG. 3, i.e., the minimum laser power to create an acoustic signal is less for AU-4 than for AS-4. Moreover, the number of cumulative acoustic events is higher for AU-4 than AS-4 for all the laser power levels tested in this example.

Example 3

Figure 4A:
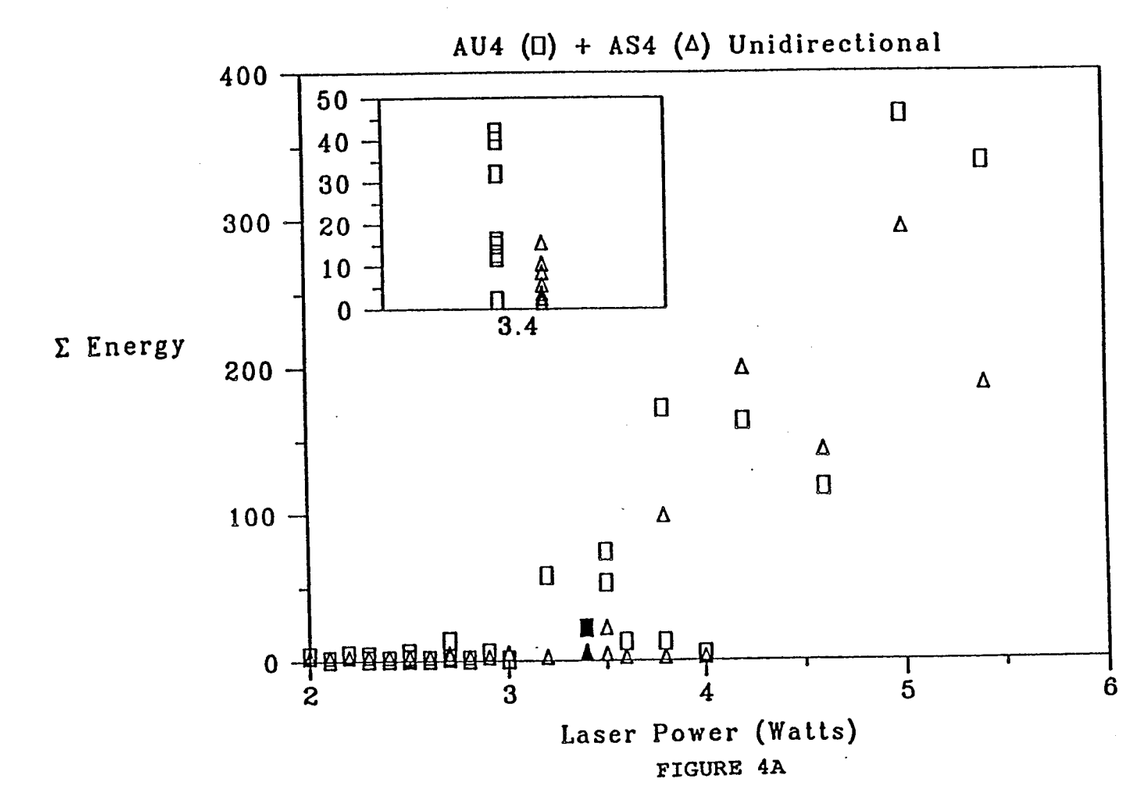
Figure 4B:
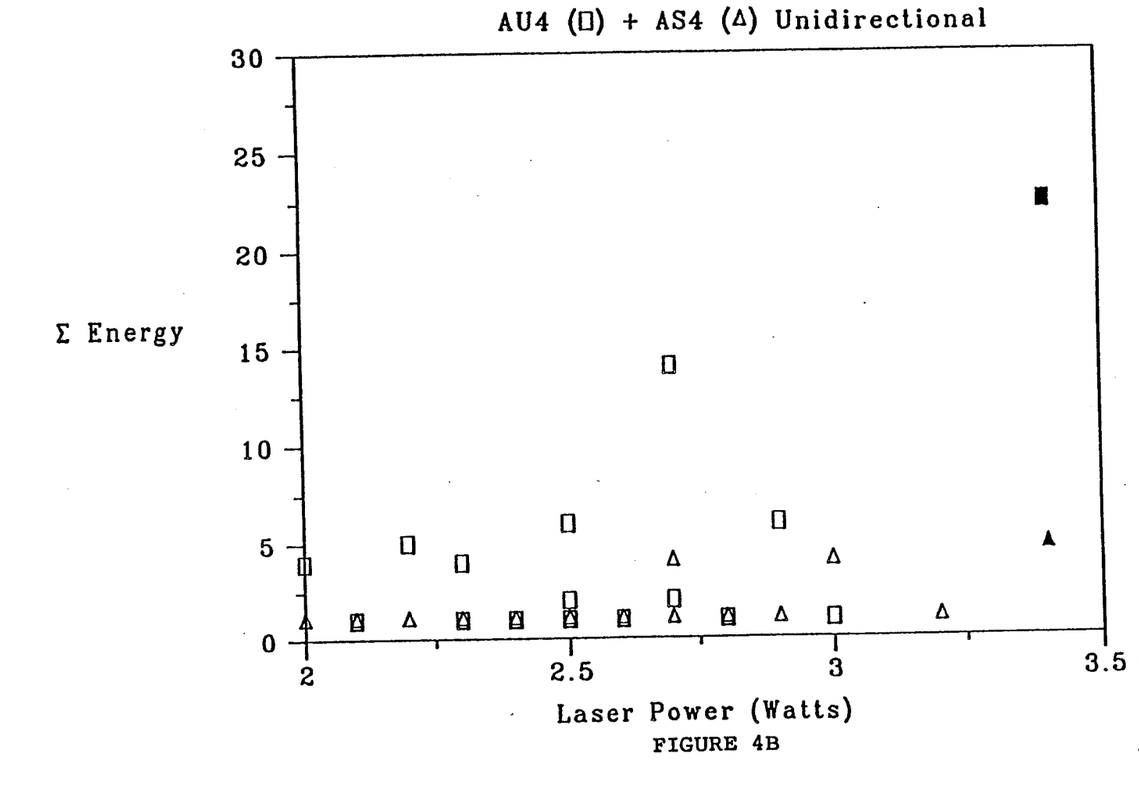

In this example unidirectional composites were subjected to the laser heating process discussed above. Plots of the emitted acoustic energy versus laser power for these tests are illustrated in FIGS. 4a and 4b.

At laser powers below 3 watts no significant acoustic energy was observed for AS-4, whereas some sporadic acoustic events with significant energy were observed for AU-4 samples. These observations are evident in FIG. 4a and more clearly illustrated in FIG. 4b which is an enlarge portion of FIG. 4a, over the laser power energy range of 2 to 3.5 watts. At the laser power of 3.4 watts, as illustrated in the insert of FIG. 4a ten repeat measurements were made and discernible differences were noted. The mean values of the acoustic energies are denoted by the two solid symbols in FIG. 4a. The distribution of all the repeat runs of these two samples indicates a significant difference in their acoustic outputs. The mean and the standard deviation at 3.4 watts were 4.7±4.8 and 22.4±14.6 for the AS-4 and AU-4 composites respectfully.

Example 4

Figure 5:
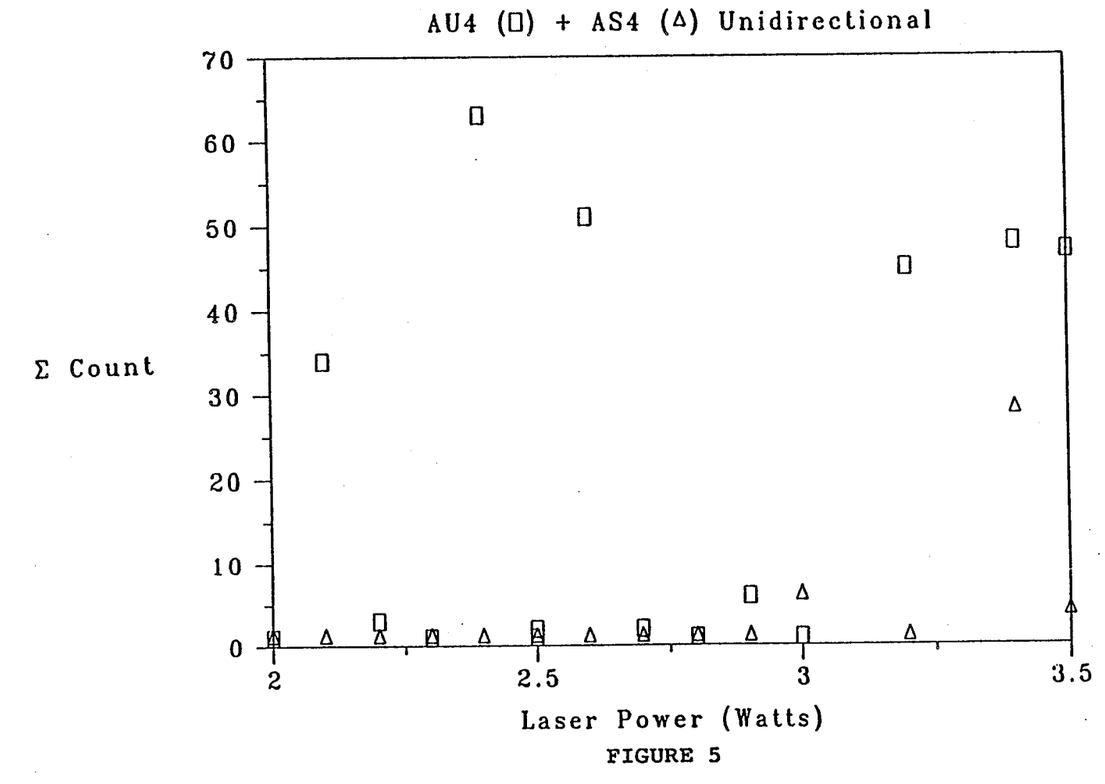

In this example, samples having a unidirectional orientation of the plys were subject to the laser heating process discussed above. In FIG. 5 the number of cumulative acoustic events is plotted versus laser power. Some sporadic acoustic events are clearly detected at laser power levels less than 3 watts for the AU-4 composites only.

Example 5

In this example unidirectional samples of AS-4 graphite fibers with Ryton ® (polyphenylene sulfide, Phillips Petroleum Co.) were also included. Ryton ® is one of the primary candidates for thermoplastic matrix composites. The unidirectional composite specimens used in this experiment were known for their poor interfacial strengths.

Figure 6:
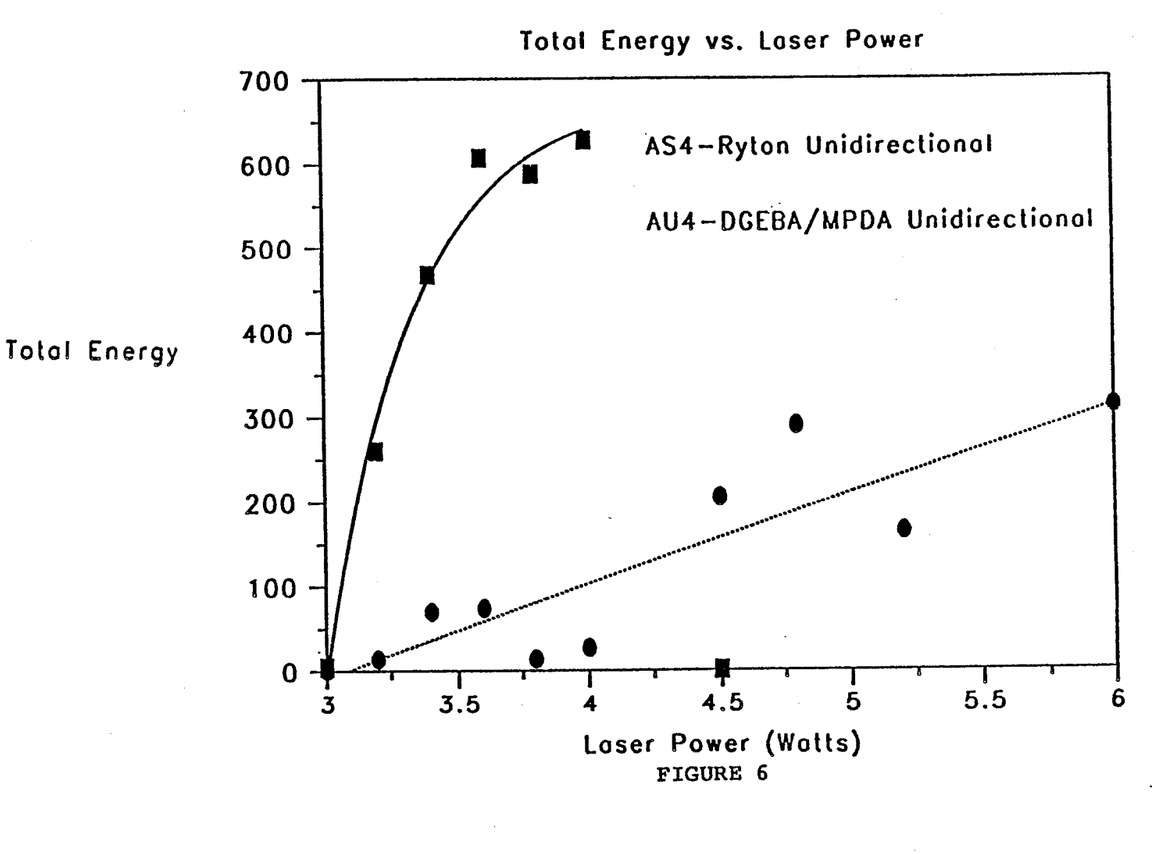

The samples were subjected to laser heating as set forth above. The laser acoustic results of the AS-4/Ryton ® sample are illustrated in FIG. 6. As compared to AU-4 epoxy, more acoustic signals were detected for the Ryton ® sample than for the AS-4/epoxy. Accordingly, the interfacial strength of AS-4/Ryton ® is inferior to that of AU-4/epoxy.

I claim:

1. A method for characterizing interface properties of a composite, which method comprises:
   (a) causing thermal debonding of an interface of said composite;
   (b) detecting debonding events that occur in step (a) and;
   (c) characterizing said interface properties of said composite from said detected debonding events.

2. A method for characterizing interface properties of a composite according to claim 1, wherein said property comprises the strength of said interface.

3. A method for characterizing interface properties of a composite according to claim 1, wherein said property comprises the strength of said interface and said interply.

4. A method for characterizing interfaced properties of a composite according to claim 1, wherein said thermal debonding in step (a) comprises heating said composite by a means selected from the group consisting of a resistance heater, an open flame, hot gases, radiative sources and combinations thereof.

5. A method for characterizing interface properties composite according to claim 4, wherein said heating means consists of a radiative source selected from the group consisting of lasers, microwaves and combinations thereof.

6. A method for characterizing interface properties of a composite according to claim 1, wherein said thermal debonding in step (a) comprises cooling said composite.

7. A method for characterizing interface properties of a composite according to claim 1, wherein said thermal debonding in step (a) comprises combinations of heating and cooling said composite.

8. A method for characterizing interface properties of a composite according to claim 1, wherein said detected debonding events of step (b) comprise acoustic emissions which result from said debonding.

9. A method for characterizing interface properties of a composite according to claim 1, wherein said detected debonding events of step (b) comprise physical changes in said composite.

10. A method for characterizing interface properties of acomposite according to claim 1, wherein said characterizing of step (c) comprises correlating said detected debonding events of step (b) with standard or reference values.

11. A method for characterizing interface properties of a composite, which method comprises:
    (a) causing thermal debonding of an interface of said composite by application of laser energy on said composite;
    (b) detecting acoustic debonding events that occur in step (a) and;
    (c) characterizing the strength of said interface debonded in step (a).

12. A method for characterizing interface properties of a composite according to claim 11, wherein said laser energy is applied to a local portion of said composite.

13. A method for characterizing interface properties of a composite according to claim 11, wherein said laser energy is scanned over an area of said composite.

14. A method for characterizing interface properties of a composite according to claim 11, wherein said laser energy is applied in a manner selected from the group consisting of periodically, cyclically, ramped, constantly and combinations thereof.

15. An apparatus for characterizing a property of a composite which comprises means for thermally debonding interface portions of a composite, means for detecting debonding events that occur during thermal debonding and means for characterizing properties of the composite which are related to the interface, said means for characterizing properties being coupled to both said means for thermally debonding and said means for detecting.

16. An apparatus for characterizing a property of a composite according to claim 15, wherein said means to thermally debond is selected from the group consisting of resistance heaters, open flames, hot gases, radiative sources, and combinations thereof.

17. An apparatus for characterizing a property of a composite according to claim 16, wherein said means to thermally debond consists of a radiative source selected from the group consisting of lasers, microwaves and combinations thereof.

18. An apparatus for characterizing a property of a composite according to claim 15, wherein said means for detecting comprises an optical sensor.

19. An apparatus for characterizing a property of a composite according to claim 15, wherein said means for characterizing properties of said composite comprises means for determining the bond strengths of the interface.

* * * * *